United States Patent
Rodriguez et al.

(10) Patent No.: US 11,001,087 B2
(45) Date of Patent: May 11, 2021

(54) METHOD AND APPARATUS FOR SINGLE PARTICLE DEPOSITION

(71) Applicants: Miguel Rodriguez, Berlin (DE); Eric Cheng, Berlin (DE)

(72) Inventors: Miguel Rodriguez, Berlin (DE); Eric Cheng, Berlin (DE)

(73) Assignee: SCIENION AG, Berlin (DE)

( * ) Notice: Subject to any disclaimer, the term of this patent is extended or adjusted under 35 U.S.C. 154(b) by 0 days.

(21) Appl. No.: 15/464,833

(22) Filed: Mar. 21, 2017

(65) Prior Publication Data
US 2017/0274689 A1    Sep. 28, 2017

(30) Foreign Application Priority Data
Mar. 23, 2016  (EP) ................................ 16000699

(51) Int. Cl.
*B41J 29/38* (2006.01)
*B41J 2/045* (2006.01)
(Continued)

(52) U.S. Cl.
CPC ............. *B41J 29/38* (2013.01); *B01L 3/0268* (2013.01); *B41J 2/04561* (2013.01); *B41J 2/04581* (2013.01); *C12Q 3/00* (2013.01); *G01N 15/1459* (2013.01); *G01N 15/1484* (2013.01); *G01N 33/4833* (2013.01); *G01N 35/1009* (2013.01);
(Continued)

(58) Field of Classification Search
CPC ................. B01L 3/0268; B01L 3/0241; B01L 2200/061; B01L 2200/0647; B01L 2200/0652; G01N 35/1016; G01N 2035/1018
See application file for complete search history.

(56) References Cited

U.S. PATENT DOCUMENTS

| 5,943,075 A * | 8/1999 | Lee | ......................... B01L 3/0268 239/102.2 |
| 5,975,682 A * | 11/1999 | Lee | ......................... B01L 3/0268 239/102.2 |

(Continued)

OTHER PUBLICATIONS

European Search Report dated Jul. 11, 2016 Based Off of Application No. 16000699.5-1371.
(Continued)

*Primary Examiner* — Brian R Gordon
(74) *Attorney, Agent, or Firm* — Grogan, Tuccillo & Vanderleeden, LLP (57) ABSTRACT

A method of depositing single particles onto a target includes loading a particle suspension to a droplet dispenser having a suspension reservoir and a nozzle section, detecting particles in the nozzle section, testing a single particle condition of the droplet dispenser, and determining whether an ejection region of the nozzle section includes one single particle. The method further includes operating the droplet dispenser for dispensing a droplet such that the droplet is dispensed onto the target if the single particle condition is fulfilled, or the droplet is dispensed into a collection reservoir if the single particle condition is not fulfilled. The step of testing the single particle condition further includes determining whether a sedimentation region adjacent to the ejection region is free of particles. A dispenser for performing the method is also provided.

11 Claims, 2 Drawing Sheets

(51) Int. Cl.

| | | |
|---|---|---|
| *G01N 33/483* | (2006.01) | |
| *G01N 15/14* | (2006.01) | |
| *C12Q 3/00* | (2006.01) | |
| *G01N 35/10* | (2006.01) | |
| *B01L 3/02* | (2006.01) | |
| *G01F 25/00* | (2006.01) | |

(52) U.S. Cl.
CPC ... *G01N 35/1016* (2013.01); *B01J 2219/0036* (2013.01); *B01J 2219/00367* (2013.01); *B01J 2219/00369* (2013.01); *B01J 2219/00468* (2013.01); *B01J 2219/00648* (2013.01); *B01J 2219/00693* (2013.01); *B01L 2200/0647* (2013.01); *B01L 2300/0663* (2013.01); *G01F 25/0092* (2013.01); *G01N 2015/1481* (2013.01); *G01N 2015/1493* (2013.01); *G01N 2035/1034* (2013.01); *G01N 2035/1062* (2013.01)

(56) References Cited

U.S. PATENT DOCUMENTS

| | | | | |
|---|---|---|---|---|
| 7,901,633 | B2* | 3/2011 | Huh | B01L 3/0241 422/403 |
| 8,282,894 | B2* | 10/2012 | Lee | B01L 3/0268 422/500 |
| 8,834,793 | B2 | 9/2014 | Koltay et al. | |
| 9,555,431 | B2* | 1/2017 | Yamaguchi | B01L 3/0268 |
| 2013/0037623 | A1 | 2/2013 | Yamaguchi | |
| 2017/0010203 | A1* | 1/2017 | Otsuka | B01L 3/0268 |
| 2017/0059590 | A1* | 3/2017 | McPeak | G01N 1/4077 |
| 2017/0241889 | A1* | 8/2017 | Otsuka | G01N 15/1484 |
| 2018/0056288 | A1* | 3/2018 | Abate | G01N 15/1459 |
| 2019/0022651 | A1* | 1/2019 | Henning | B01L 3/502707 |
| 2019/0025185 | A1* | 1/2019 | Katoh | B01L 3/0268 |

OTHER PUBLICATIONS

Azmi Yusof et al: "Inkjet-like printing of single-cells", Lab on a chip: Miniaturisation for chemistry, physics, biology, materials science and bioengineering, vol. 11, No. 14, Jun. 9, 2011, p. 2447.
Andre Gross et al: "Single-Cell Printer: Automated, On Demand, and Label Free", Journal of Laboratory Automation Society for Laboratory Automation and Screening, Dec. 1, 2013, pp. 502-518.
Andre Gross et al: "Technologies for Single-Cell Isolation", Int. J. Mol. Sci 2015, 16, 16897-16919.
Eric Cheng et al: "Investigation of the hydrodynamic response of cells in drop on demand piezoelectric inkjet nozzles", Biofabrication 8 (2016) 015008.
S. Yamaguchi, A. Ueno, Y. Akiyama, and K. Morishima, "Cell patterning through inkjet printing of one cell per droplet," Biofabrication, vol. 4, No. 4, p. 045005, 2012.
R. The, S. Yamaguchi, A. Ueno, Y. Akiyama, and K. Morishima, "Piezoelectric inkjet-based one cell per one droplet automatic printing by image processing," in 2013 IEEE/RSJ International Conference on Intelligent Robots and Systems, 2013, pp. 502-507.
A. Yusof, R. Zengerle, and P. Koltay, "Towards a microfluidic dispenser chip for printing of single cells," in 2011 IEEE 24th International Conference on Micro Electro Mechanical Systems, 2011, pp. 1059-1062.
I. Leibacher, J Schoendube, J. Dual, R. Zengerle, and P. Koltay, "Enhanced single-cell printing by acoustophoretic cell focusing", Biomicrofluidics, vol. 9, No. 2, p. 024109, Mar. 2015.
A. M. Yusof and P. Koltay, "A Non-invasive Single Cell Dispensing Approach for 2-Dimensional Micro-Patterning," 12th International Conference on New Actuators, 2010, pp. 1033-1036.
E. Cheng, A. Ahmadi, and K. C. Cheung, "Investigation of the Hydrodynamics of Suspended Cells for Reliable Inkjet Cell Printing," p. V001T03A010, Aug. 2014.
Alexander Waidmann; Concept study on the subject: Dosing of single cells; Hochschule Offenburg University of Applied Sciences; Mar. 2008 with partial machine translation—pp. 10 to 28.

* cited by examiner

METHOD AND APPARATUS FOR SINGLE PARTICLE DEPOSITION

CROSS REFERENCE TO RELATED APPLICATIONS

This application claims the benefit of, and incorporates by reference in its entirety, European Patent Application No. 16 000 699.5, filed on Mar. 23, 2016.

BACKGROUND

The invention relates to a method of depositing single particles with a droplet dispenser, e.g. a piezoelectric dispenser, onto a target, in particular to a method of dispensing droplets including particles, wherein droplets including single particles are deposited onto the target if a single particle condition of the droplet dispenser is fulfilled. Furthermore, the invention relates to a dispenser apparatus, being adapted for dispensing droplets including single particles onto a target. Applications of the invention are available in particular in the fields of biochemistry, biology and medicine, e.g. for handling single biological particles, like biological cells.

A plurality of technologies for single-cell isolation, e.g. for handling of single cells in biotechnology and medicine, have been described by A. Gross et al. in "Int. J. Mol. Sci." (2015, 16, 16897-16919), like e.g. flow cytometry, manual cell picking, microfluidic techniques, and inkjet-like single-cell printing. A single-cell printer comprises e.g. a microfluidic dispenser integrated in a polymer cartridge. Droplets of a cell suspension included in the dispenser are deposited on a target substrate. Single-cell printing has advantages in terms of flexibility and easy interfacing with other upstream and downstream methods. However, single-cell printers have to be controlled such that each droplet deposited onto the target includes one single cell only.

Controlling the single-cell printer has been described e.g. by A. Gross et al. in "Journal of Laboratory Automation" (2013, 18(6) 504-518) and by A. Yusof et al. in "Lab Chip" (2011, 11, 2447). An imaging system and automated object recognition algorithms are used for detecting and classifying cells in the microfluidic dispenser chip during dispensing operation and for testing whether a single particle condition of the droplet dispenser is fulfilled. According to A. Gross et al., the single particle condition is fulfilled if a volume at the dispenser orifice equal to a droplet volume includes one single cell. In this case, a droplet is dispensed to the target, while droplets containing no cell or multiple cells are deflected in flight towards a waste container by vacuum suction. A. Yusof et al. use a dispenser which is moved from a waste container to a target if an ejection region near the nozzle orifice includes one single cell only.

Practical applications of the conventional techniques of controlling a single-cell printer have the following disadvantages. Firstly, the single-cell printing has a low yield. Despite of using the imaging system and object recognition algorithms, only 80% to 85% of droplets deposited onto the target include single cells only. The remaining droplets include more than one cell or no cell. Furthermore, the application of the conventional controlling techniques is restricted to the particular types of dispenser, cell suspension and operation conditions used by the authors of the above publications. Using another dispenser or other materials requires other object recognition and control algorithms.

The hydrodynamic response of cells in piezoelectric nozzles has been characterized by E. Cheng et al. in "Biofabrication", vol. 8, 2016, p. 015008. Cell motion has been studied by high-speed imaging and cell tracking. However, concepts for single-cell printing have not been described by E. Cheng et al.

BRIEF DESCRIPTION

The objective of the invention is to provide an improved method of depositing single particles with a droplet dispenser onto a target, being capable of avoiding disadvantages of conventional techniques. In particular, the objective of the invention is to provide the single particle depositing method with improved yield and reproducibility, and/or with an extended applicability with different types of droplet dispensers, particles suspensions and/or operation conditions. Furthermore, the objective of the invention is to provide an improved dispenser apparatus for dispensing single particle droplets onto a target, being capable of avoiding disadvantages of conventional techniques.

The above objectives are solved by a method of depositing single particles onto a target and a dispenser apparatus correspondingly comprising the features of the independent claims. Advantageous embodiments of the invention are defined in the dependent claims.

According to a first general aspect of the invention, the above objective is solved by a method of depositing single particles with a droplet dispenser onto a target. The droplet dispenser, preferably comprising a Piezo Dispense Capillary (PDC), includes a suspension reservoir, a drive unit and a nozzle section. At least the nozzle section is made of an optically transparent material. A particle suspension is loaded to the droplet dispenser, so that the nozzle section and at least a portion of the suspension reservoir is filled with the particle suspension. The particle suspension comprises a fluid, like e.g. water or a physiological salt solution or another encapsulating fluid, and particles of one or multiple type(s) with one or multiple size(s).

The particles in the nozzle section, which preferably has an inner shape tapered in downstream direction, are detected, using an imaging device, preferably a nozzle camera arranged adjacent to the nozzle section. Detecting the particles preferably comprises imaging the nozzle section, in particular the lower extremity of the PDC, recognizing the particles and providing the particle positions within the nozzle section image.

A single particle condition of the droplet dispenser is tested. Preferably, the nozzle section image is subjected to the testing step. An ejection region of the nozzle section and a sedimentation region (or: sedimentation layer) adjacent to the ejection region are analysed. The ejection region is a portion at the downstream end of the nozzle section opening at the nozzle orifice to the surrounding. The size of the ejection region is characterized by the volume thereof or, as the nozzle typically has an axial symmetry, by an axial height thereof. The ejection region has a size such that particles in the ejection region exit the nozzle section with an ejected droplet. Preferably, the ejection region is determined by a mapping procedure as outlined below. The sedimentation region is a portion of the nozzle section directly above the ejection region on the upstream side thereof. The size of the sedimentation region, i.e. the volume or axial thickness thereof, is defined such that particles included in the sedimentation region are displaced into the ejection region by sedimentation immediately before the dispensing operation, in particular during a predetermined operation delay interval between the steps of detecting the particles and operating the droplet dispenser.

If the ejection region includes one single particle and the sedimentation region is free of particles (or: the sedimentation region includes the suspension fluid only), the single particle condition is fulfilled. If the ejection region does not include any particles, and/or the sedimentation region includes at least one particle, and/or the ejection region includes multiple particles, the single particle condition is not fulfilled.

The droplet dispenser is operated for dispensing droplets. A current droplet is dispensed (or: "printed") onto the target (encapsulation of single particle), if the single particle condition is fulfilled, i. e. if the ejection region includes one single particle. The target comprises a substrate, which is adapted for accommodating the droplet with the single particle, e.g. a multi-well plate and/or a microwell plate. Alternatively, the current droplet is dispensed into a collection reservoir, if the single particle condition is not fulfilled. Preferably, the collection reservoir is a vessel which is configured for accommodating droplets without or with multiple particles, in particular for discarding or optionally re-using in further process steps.

At least one of the droplet dispenser and the target and the collection reservoir is movable, so that the droplet dispenser and the target can be adjusted relative to each other. Adjusting the droplet dispenser and the target relative to each other for dispensing the single particle droplet requires a predetermined time, i.e. the operation delay interval between the steps of detecting the particles and operating the droplet dispenser for single particle deposition, wherein the operation delay interval depends on the distance between the locations of detecting the particles and single particle deposition and in particular the size of and dispensing position on the target and the speed of mutual movement. Advantageously, the consideration of the sedimentation region in the testing step essentially improves the yield of the single particle deposition.

According to a further preferred embodiment of the invention, a negative control mode can be conducted for dispensing a reference sample droplet, which is empty of cells. Advantageously, this allows e.g. the detection of ambient foreign materials, like DNA/RNA content of a solution and improves the validity of the data obtained with the single cells.

According to another embodiment of the invention, at least one geometric feature of the particle in the ejection region can be detected, and the step of testing the single particle condition further includes determining whether a particle in the ejection region fulfils predetermined geometric conditions, preferably with regard to circularity and elongation and area factor. This embodiment may have advantages for single cell reliability and for excluding cell doublets or aggregates from dispensing.

According to a second general aspect of the invention, the above objective is solved by a dispenser apparatus, which is adapted for dispensing droplets onto a target. The dispenser apparatus comprises at least one droplet dispenser, preferably a PDC, having a suspension reservoir, a drive unit and a nozzle section, being carried by a dispenser head and being controlled by a control device. Furthermore, the dispenser apparatus comprises a nozzle camera being arranged for imaging the nozzle section and for detecting particles in the nozzle section. Preferably, an irradiation device, e.g. an LED device is provided, which is adapted for illuminating the nozzle section, so that the particle detection can be improved. Advantageously, the irradiation device provides a stable and consistent light source adapted to the nozzle camera.

A testing unit is provided in communication with the nozzle camera and with the control device. The testing unit is adapted for testing whether the ejection region of the nozzle section includes one single particle or not and the sedimentation region of the nozzle section is free of particles or not. The control device is adapted for operating the droplet dispenser and dispensing a droplet such that the droplet is dispensed onto the target, if the nozzle section includes one single particle and the sedimentation region of the nozzle section is free of particles, or the droplet is dispensed into a collection reservoir, if the nozzle section includes no or multiple particle(s).

As the main advantage of the invention, testing the single particle condition is extended from the ejection region to the sedimentation region. Contrary to the conventional techniques, not only the ejection region is tested, but also the neighbourhood thereof, which may include particles travelling into the ejection region after detecting the particles and testing the single particle condition and before dispensing the droplet. Accordingly, the yield and reproducibility of dispensing single particles can be essentially improved.

With more details, a single particle dispensing system, preferably for a PDC, is proposed which facilitates predictive single particle encapsulation by optical feedback and modeling of individual particle's behaviours within the nozzle section. In particular through a priori training of the particle's behaviours within the PDC, the optical system can accurately identify single particles which possess a high probability of encapsulation in a proceeding droplet. Once a particle has been identified, the testing unit provides feedback to the droplet dispenser and the drive unit thereof to selectively deposit the cell encapsulated droplet while discarding all other remaining droplets.

According to a preferred embodiment of the invention, image data of the ejection region and the sedimentation region are pre-stored in the testing unit. Advantageously, this facilitates conducting the testing step by comparing a current image of the nozzle section during the operation of the dispenser apparatus with the pre-stored image data. The image data may comprise fixed sets of ejection region image data and sedimentation region image data if the dimensions of the ejection region and the sedimentation region do not change during the operation of the dispenser apparatus. Alternatively, the image data may include multiple sets of ejection region image data and/or sedimentation region image data if the dimensions of these sections dynamically change during the operation as a result of changing dispensing conditions.

Preferably, the testing unit is integrated in the control device of the dispenser apparatus. Advantageously, this facilitates the control of the droplet dispenser. Particularly preferred, the testing unit includes an image data storage, which is adapted for accommodating and optionally updating the image data of the ejection region and the sedimentation region, and an image processing unit, which is adapted for a particle recognition.

According to a particularly preferred embodiment of the invention, preparing steps are provided, which are conducted before the operation of the dispenser apparatus for depositing the single particles on the target. The preparing steps include identifying the ejection region and the sedimentation region for the particular dispensing operation to be conducted.

Advantageously, the preparing steps provide an autonomous mapping pre-process including the detection of the particle motion upstream the ejection region. Accordingly, a single particle dispensing platform with increased reliability and minimized false positive droplets is provided. As an advantageous example, test printing was performed using a watery suspension of polystyrene beads having an average diameter of 14.8 μm and a density of 500,000 particles/ml. Imaging of the grid post-printing successfully demonstrated the improved feedback capability of the dispenser apparatus to provide near 100% single particle encapsulation rates. This result was obtained with mammalian cells as well.

Particularly preferred, the preparing steps include a step of mapping the nozzle section, including an identification of the ejection region, and determining, e.g. calculating or measuring (mapping), the sedimentation region on the upstream side of the sedimentation region. Preferably, the mapping of the nozzle section includes an analysis of the detected particles in the nozzle section such that a travel region and the ejection region are assigned to portions of the nozzle section. The travel region is identified as a portion of the nozzle section, in which the particles are displaced during the dispensing operation of the droplet dispenser, i.e. during activating the drive unit of the droplet dispenser without leaving the nozzle section. On the other hand, the ejection region is identified as a portion near the orifice of the nozzle section which is left by the particles during the operation of the droplet dispenser.

With a particularly preferred implementation of the invention, the mapping step includes a training operation of the droplet dispenser. During the training operation, a series of droplets is dispensed, while the particles are detected and tracked in between each dispensing operation. A first group of particles is identified, which are displaced within the nozzle section during activating the driving unit, and a second group of particles is identified, which are ejected from the nozzle section during the activation of the driving unit. The populated map highlights two distinct regions within the nozzle section. The volumes accommodated by the first and second groups of particles are correspondingly identified as the travel and ejections regions. The training operation is conducted with a particle suspension to be applied in a subsequent single particle deposition process or with a test suspension having equal or similar properties like the particle suspension to be deposited.

Determining the sedimentation region preferably includes a calculation resulting in an estimation of those particles, which are displaced from the travel region to the ejection region by the effect of sedimentation during the operation delay interval between the testing and dispensing steps. The sedimentation region is calculated in dependency on parameters of the particle suspension, in particular a viscosity of the suspension fluid, a diameter of the particles and a mass of the particles, and further in dependency on the operation delay interval, in particular on the distance between the position of the droplet dispenser at the collection reservoir and the position of the droplet dispenser at the target, the processing speed of detecting the particles and conducting the testing step, and the speed of moving the droplet dispenser between both positions.

Alternatively, determining the sedimentation region is based on a measurement thereof, including a mapping using an automatic analysis of particle behaviour inside the PDC.

The inventors have found that the volume of the ejection region is not equal to the volume of a droplet dispensed. Firstly, it can be calculated that e.g. for spherical particles with a diameter in a range of about 10 μm to 20 μm, there is an initial lag in the particle's motion relative to the fluid's motion, causing a decoupling of the particles and the fluid displacement during droplet formation. Furthermore, the fluid flow field within the nozzle section during droplet ejection is complex, so that making a reliable model of the volume that would constitute the droplet would be computationally difficult and impractical. Accordingly, the preparing steps, in particular the mapping step represents a further advantageous difference over the conventional techniques. By the direct observation and classification of the particles via the mapping pre-processing step, an accurate model of the nozzle section can be provided without complex calculations.

With more details, the optical feedback algorithm is trained through an autonomous setup procedure which maps out particle behavioural regions of the PDC within the nozzle camera's field of view. This procedure can be performed for every new PDC, printing parameter or cell suspension utilised. Thus, creating a unique map for each new printing operation which allows for a more accurate optical feedback system for single particle encapsulation. During the dispensing operation, the optical feedback system can dynamically update the map if necessary to compensate for any shifts in the printing parameters.

Advantageously, the sedimentation region can be calculated in two different ways. According to a first variant, a single static calculation is conducted, using one single set of parameters of the particle suspension and the operation delay interval. Advantageously, the static calculation saves computational time and reduces the response time of the droplet dispenser. According to a second variant, multiple dynamic calculations of the sedimentation region are conducted, using changing sets of the parameters of the particle suspension and the operation delay interval. As an example, the average diameter of the particles and/or the distance between the droplet dispenser positions at the collection reservoir and the target, in particular a deposition site at the target, can vary. For each set of those parameters another size of the sedimentation region is calculated. Advantageously, the dynamic calculations provide a more accurate model for testing the single particle condition.

According to a further preferred embodiment of the invention, the droplet dispenser is located at the collection reservoir, while the testing step is performed. Droplets are dispensed into the collection reservoir, and particles in the nozzle section are detected and the single particle condition is tested with each dispensing operation. If the single particle condition is fulfilled, i.e. if the ejection region includes one single particle only and the sedimentation region is free of particles (the sedimentation region consists of the fluid only), the droplet dispenser is moved to the target or the target is moved to the droplet dispenser (e.g. to a position between the droplet dispenser and the collection reservoir), and the droplet including the single particle is dispensed onto the target. If the droplet dispenser is moved to the target, this has advantages in terms of applying the invention with an available dispenser apparatus including a moveable dispenser head. Advantageously, all droplets including multiple particles can be discarded or optionally collected in the collection reservoir for a subsequent use.

Preferably, the droplet dispenser is moved with the moveable dispenser head between the collection reservoir and the target. Advantageously, the dispenser head can be provided with a head camera being directed onto the target. The head camera is adapted for collecting images of the target, in particular of the deposition portion of the target so that the dispensing result can be checked. In addition for verifying the presence of a single particle dispensed onto the target, the head camera can be used for an automatic target alignment of the droplet dispenser and an alignment for improved dispensing precision, e.g. in micro-wells.

A further important advantage of the invention results from the broad range of particle types, which are suitable for the application of the inventive single particle deposition method. In particular, the particle may comprise at least one of a biological particle and a synthetic particle. Biological particles may comprise e.g. biological cells, cell aggregates, cell organelles and/or cell components. Synthetic particles may comprise e.g. glass or polymer beads. The particle suspension in the droplet dispenser may include one single type of particles or a mixture of multiple types of particles. All particles may have the same dimension, e.g. cross-sectional size, and shape, e.g. a spherical shape or an elongated shape, or the particles may have a size distribution with a characteristic average dimension and/or different shapes, e.g. irregular shapes. Preferably, the particles have a characteristic dimension of at least 5 µm and/or most 60 µm. The particles may include a marker substance, like e.g. a fluorescing pigment, for facilitating the particle detection in the nozzle section by contrast enhancement. In this case, the irradiation device can be adapted for exciting the marker substance.

DRAWINGS

Further details and advantages of the invention are described in the following with reference to the attached drawings, which show in.

DETAILED DESCRIPTION

Features of preferred embodiments of the invention are described in the following with exemplary reference to a dispenser apparatus including at least one PDC, like e.g. the apparatus sciFLEXARRAYER (manufacturer: Scienion AG, Germany). It is emphasized that the application of the invention is not restricted to this particular model or PDC-based systems, but rather correspondingly possible with other types of non-contact droplet dispensers, like e.g. solenoid valve controlled dispensers. Furthermore, particular reference is made in the following to the application of the inventive single particle depositing method and the adaptation of the dispenser apparatus for implementing the method. Details of a dispenser apparatus, which are known from conventional systems, are not described. Furthermore, exemplary reference is made to dispensing droplets including single biological cells. The application of the invention is not restricted to dispensing single cells, but correspondingly possible with other biological or non-biological particles.

Figure 1:
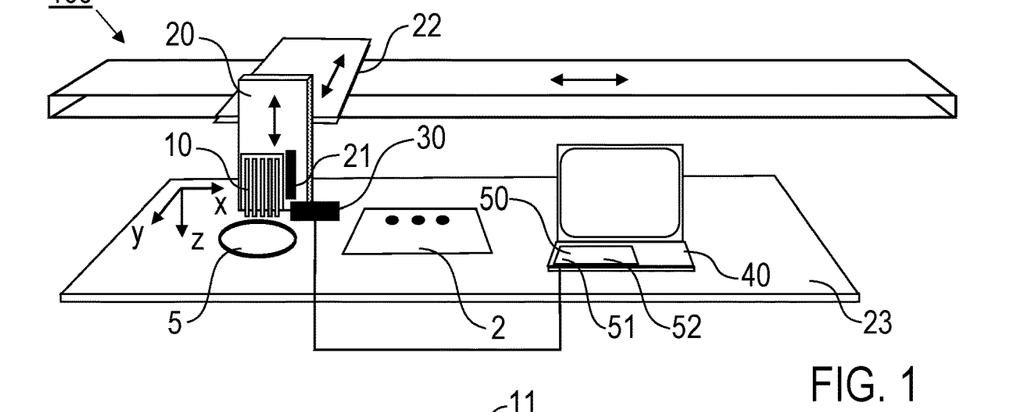
FIG. 1: a schematic view of features of a dispenser apparatus according to preferred embodiments of the invention.

FIG. 1 schematically illustrates an embodiment of a dispenser apparatus 100, which is adapted for dispensing droplets including single particles, like single biological cells, onto a target 2. The dispenser apparatus 100 comprises at least one droplet dispenser 10, which is attached to a dispenser head 20. With practical examples, one single droplet dispenser 10 or a line or matrix array of droplet dispensers 10 can be provided.

The at least one droplet dispenser 10 is a PDC, including a suspension reservoir 11 and a nozzle section 12 (see FIG. 2) as well as a piezo-electrically activated drive unit 110 (FIG. 1). With more details, the droplet dispenser 10 is composed of a glass capillary connected to a syringe pump (not shown) for sample loading and washing between different samples. The drive unit includes a piezo-ceramic element positioned around the glass capillary. By applying a control voltage to the piezo-ceramic element, a dispensing operation of the droplet dispenser is triggered.

The dispenser head 20 onto which the droplet dispenser 10 is mounted is moveable with a translation stage 22. The translation stage 22 is adapted for translations of the dispenser head 20 in all three spatial directions (x-, y- and z-directions). The target 2 and a collection reservoir 5 are arranged in the operation range of the translation stage 22, e.g. on the common platform 23. The position of the dispenser head 20, i.e. the position where droplets are dispensed, is controlled via the movement of the dispenser head 20 using the translation stage 22 over the platform 23, in particular to the target 2 or the collection reservoir 5. Alternatively, the at least one dispenser 10 can be arranged with a fixed position, while the target 2 is mounted on a translation stage for adjusting the target position relative to the droplet dispenser position. According to another alternative, both of the at least one dispenser 10 and the target 2 can be moveable with translation stages being adapted for translations along the three or less spatial directions.

Figure 4:
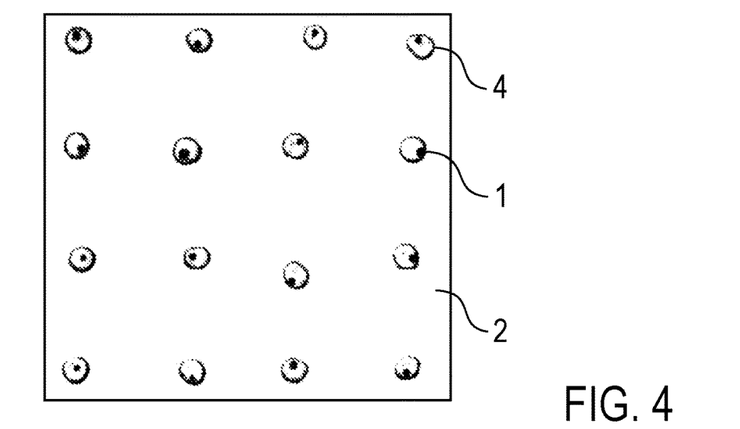
FIG. 4: a photographic image of a target carrying droplets with single particles.

A head camera 21 is mounted on the dispenser head 20. It can be coupled to a range of different light sources (not shown). The head camera 21 is adapted for both of the alignments of the target 2 and the droplet dispenser 10 relative to each other and for quality control of the deposition result. To this end, the head camera 21 is coupled with the control device 40 running an image analysis software, like "Online Array QC". After the droplet deposition on the target 2, the head camera 21 can be used for visualizing the printed droplets 4 including the single particles 1 (see FIG. 4). If necessary, the head camera 21 is used for identifying the number of particles present at the different deposition positions. Optionally, a fluorescence exciting light source can be used for illuminating the target, so that particles carrying a marker substance, e.g. fluorescently labelled cells, can be visualized and detected.

The dispenser apparatus 100 is adapted for conducting the detecting and testing steps with the at least one droplet dispenser 10 while it is operated at the collection reservoir 5. A nozzle camera 30 is placed over the platform 23 adjacent to the droplet dispenser 10 under consideration such that the nozzle section of the at least one droplet dispenser 10 can be imaged and particles in the nozzle section can be detected with the nozzle camera 30. Optionally, a light source (not shown) can be arranged for illuminating the droplet dispenser 10. As an example, a UV light source can be used for illuminating the nozzle section 12, so that the detection of e.g. the fluorescently labelled cells can be improved.

Figure 2:
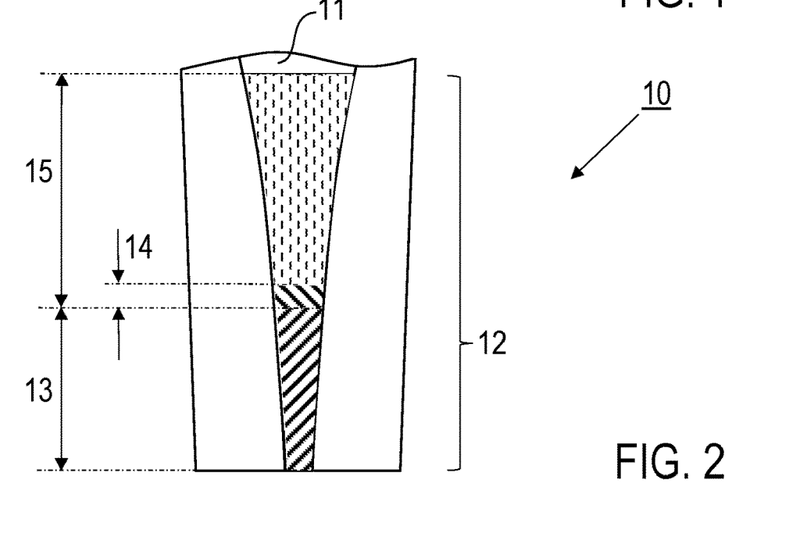
FIG. 2: a schematic cross-sectional view of a nozzle section with an illustration of the ejection region, the sedimentation region and the travel region.

The nozzle camera 30, like e.g. the camera IDS UI2220 SE, is provided with a CCD-based device and a camera optic, and it is configured for imaging the nozzle section 12 and further for a visualization and monitoring of the drop formation prior to dispensing. As an example, the nozzle camera 30 is adapted for detecting particles in the nozzle section of the droplet dispenser 10 over an axial length of e.g. 700 µm to 800 µm. The nozzle camera 30 is connected with the control device 40 including the image processing unit 52. Using the location information on the particles and the a priori knowledge of the particle behaviour within the nozzle section 12, the single particle condition of the droplet dispenser can be analysed as outlined below.

If multiple droplet dispensers are provided, the nozzle camera 30 is arranged for collecting images of all droplet dispensers. Alternatively, multiple nozzle cameras can be provided for collecting images of single droplet dispensers or groups of droplet dispensers, or one nozzle camera can be adjusted relative to one of the droplet dispensers.

Optionally, geometric properties of identified cells for selective dispensing can be detected with the nozzle camera 30. Measuring the physical appearance of a cell within the nozzle, in particular the ejection region, allows for a more selective dispensing criteria. The cell properties measured includes circularity, elongation and area. Circularity is calculated by the ratio of the identified cell's perimeter divided by the perimeter of a perfect circle of equivalent area. A perfect circle will have a circularity of 1 with the circularity factor increasing in value as a cell appears to be more distorted (i.e. having non-smooth edges). The elongation factor is the ratio of the length of the major axis of a cell divided by the length of the perpendicular axis at the particle's center. Again, a perfect circle will have an elongation factor of 1 while ellipsoid shapes will have larger values. The area of a particle is the total number of pixels in which the identified cell is made up of.

Consideration of these parameters may have advantages for single cell reliability as it could be used to identify cell doublets or aggregates and rejected from printing.

For example, a set of identified particles can be plotted with their circularity factor against its elongation factor. From this plot, it is apparent that circular single cells aggregate around values of circularity=1 and elongation=1 with distorted particles further away in the graph. Therefore, a decision boundary to print can be drawn based on these two factors. Particles below the decision boundary are accepted to print and particles above the decision boundary are rejected. The decision boundary is user defined and customisable depending on the user's objectives.

The area factor along with the circularity and elongation factor is useful in some cases for consideration in sequencing applications as it can be used as an indicator of cell state. As an example, a cell appearing larger than normal could be an indicator of a cell undergoing apoptosis and should be excluded from sequencing. A minimum and maximum area is user defined and sets a range of acceptable cell sizes to be printed. Any cells with an area outside of the user defined minimum or maximum is rejected from printing.

Furthermore, the dispenser apparatus 100 includes a control device 40, which is arranged for controlling the operation of the at least one droplet dispenser 10. To this end, the control device 40 comprises a computer circuitry which is connected with the drive unit of the at least one droplet dispenser 10 and the translation stage 22 as well as the nozzle and head cameras 30, 21. The control device 40 includes a testing unit 50, which is adapted for testing the single particle condition of the at least one droplet dispenser 10. To this end, the testing unit 50 is coupled with the nozzle camera 30 and provided with an image data storage/memory device 51 storing image data of the at least one droplet dispenser 10 and with an image processing unit 52, which identifies the presence and location of any particle within the nozzle section of the at least one droplet dispenser 10.

FIG. 2 schematically illustrates the downstream end of a droplet dispenser 10, including the suspension reservoir 11 (partially shown) and the nozzle section 12. The droplet dispenser 10 comprises e.g. a glass capillary with an inner diameter of about 40 μm to 90 μm. The nozzle section 12 includes the ejection region 13 and the travel region 15, which are identified in preparing steps by the particle behaviour during the dispensing operation. The ejection region 13 is identified as the volume, which covers all positions of particles, which are ejected during a single dispensing operation. The travel region 15 is identified as covering all positions of particles, which are displaced during a single dispensing operation, while being kept within the droplet dispenser 10.

The particles are displaced during the dispensing operation due to the movement of the fluid within the nozzle section 12. Additionally, particles are displaced due to sedimentation from the travel region 15 to the ejection region 13. Accordingly, a sedimentation region 14 is defined, which is the downstream section of the travel region 15. The sedimentation region 14 covers all positions of particles, which can be displaced by the effect of gravity during the time interval between the particle detection and the dispensing operation, including a duration of the movement of the droplet dispenser 10 from the collection reservoir 5 to the target 2.

The volume of the sedimentation region 14, in particular the height in axial direction of the droplet dispenser 10 is calculated on the basis of the following considerations. The sedimentation velocity (v) of a particle is driven by gravity, and it can be calculated by:

$$v = \frac{(\rho_p - \rho_f)gD^2}{18\mu}$$

wherein $\rho_p$ is the mass density of the particle, $\rho_f$ is the mass density of the fluid, g is the gravitational acceleration, D is the dimension, e.g. diameter of the particle and μ is the dynamic viscosity of the fluid.

The displacement distance is calculated by the product of the sedimentation velocity and the time required for the dispenser apparatus 100 to test the single particle condition and to move the droplet dispenser 10 to the target 2. In practice, the time for testing the single particle condition is negligible compared with the movement time, which is provided by the dispenser apparatus 10, in particular the speed of the translation stage 22.

Typically, the particle density is larger than the fluid density, so that all particles within the nozzle section 12 will sediment over time. Only particles near the upstream boundary of the ejection region 13 within the sedimentation region 14 are critical for the consideration of the single particle condition. Accordingly, the sedimentation region 14 is always adjacent to the ejection region/travel region boundary.

The size of the sedimentation region 14 can be calculated in a static or in a dynamic way as follows.

For the static calculation, the variables in the above equation are generalized by taking an average particle diameter and the maximum time required for the dispenser apparatus 100 to reach a desired target 2. Accordingly, one fixed sedimentation region 14 is determined.

With a practical example of a cell suspension, the values are as follows: $\rho_p$=1068 kg/m$^3$, $\rho_f$=1000 kg/m$^3$, g=9.8 m/s$^2$, and μ=1 mPa·s. An average cell diameter of D=18 μm and a duration for moving the droplet dispenser 10 to the target 2 of 5 s would yield a thickness of the sedimentation region of about 60 µm. The above calculation has been done on the assumption that the particles do not contact the inner wall of the PDC channel. This approach is fulfilled in practice.

For the dynamic calculation, the values of $\rho_p$, $\rho_f$, g and µ are assumed to be constant. However, the diameter D and the time to target 2 are variables. The time to target 2 can be provided by the dispenser apparatus 100 as the desired target locations are predefined before the dispensing operation. The diameters D can be estimated by the apparent diameter of the particles as identified with the nozzle camera 30. Accordingly, different dimensions of the sedimentation region 14 are obtained for different diameters D and time to target 2 values. Accordingly, for each particle outside the ejection region 13 and within the field of view of the nozzle camera 30, a unique sedimentation region 14 can be determined. Advantageously, this results in a more robust consideration of the single particle condition, especially for particle samples, which have wide particle size distributions. As there is a $D^2$ relation to the sedimentation velocity, a particle of e.g. 12 µm will only have a sedimentation velocity of 5.3 µm/s, while a particle of e.g. 18 µm will have a corresponding sedimentation velocity of 11.9 µm/s.

Figure 3:
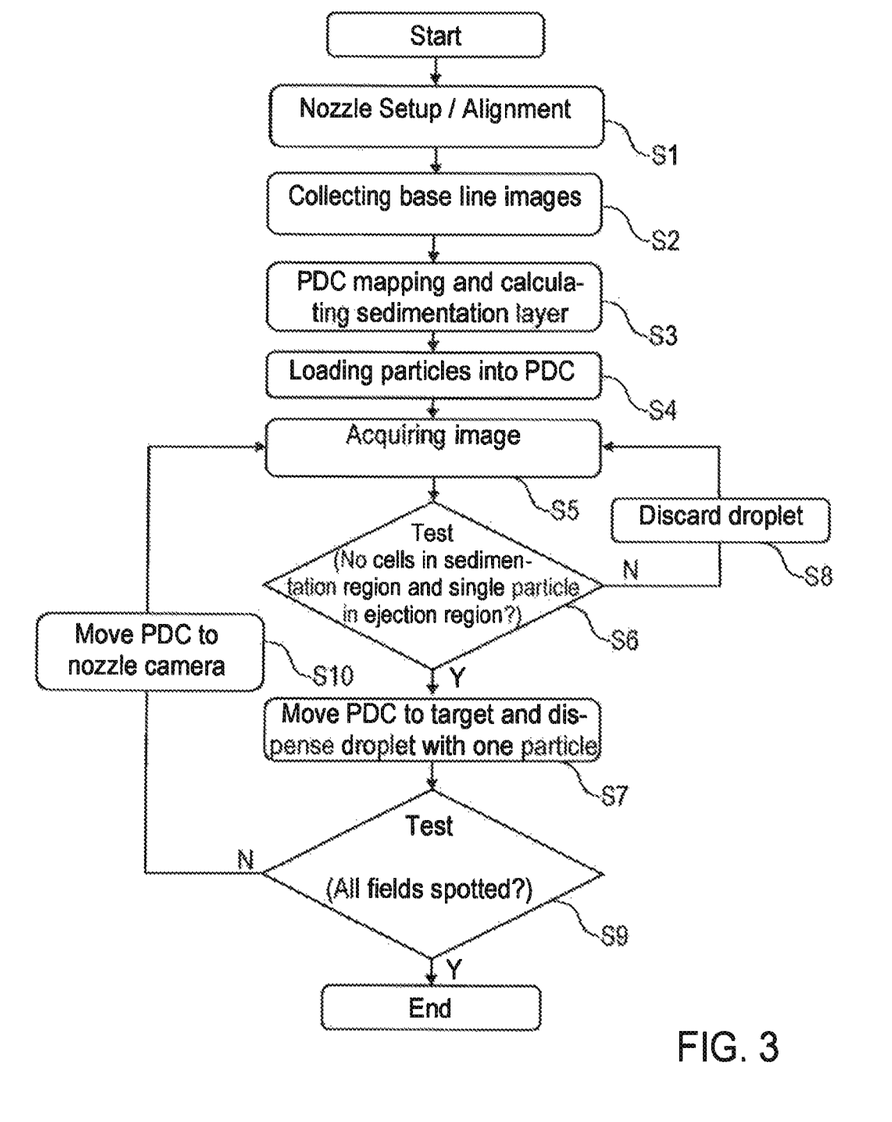
FIG. 3: a flow chart illustrating features of preferred embodiments of the inventive single particle depositing method.

FIG. 3 illustrates a flow chart representing features of preferred embodiments of the inventive single particle deposition method. After the start of the procedure, a nozzle setup and alignment (step S1) and a step of collecting base line images (step S2) are conducted. With step S1, the droplet dispenser 10 is aligned relative to the collection reservoir 5 and the nozzle camera 30 at the fixed position on the platform 23 (see FIG. 1). Collecting base line images with step S2 includes the collection of images of the nozzle section 12, in particular the ejection region 13 and the downstream end of the travel region 15 thereof (see FIG. 2).

Subsequently, mapping of the nozzle section 12 of the droplet dispenser 10 and calculating the sedimentation region 14 are conducted with step S3. The mapping step includes an identification of the ejection and travel regions 13, 15 for the particular sample and dispensing parameters to be used. Multiple dispensing operations are conducted with particles or test beads having similar properties like the particles to be deposited. The number of training dispensing operations is e.g. 200 to 300 droplets. The sedimentation region 14 is calculated on the basis of one of the above static or dynamic calculation methods.

The ejection and travel regions 13, 15 are identified by tracking and characterization of a number of particles as they pass through the nozzle section 12 during the dispensing operation. As droplets are produced by the droplet dispenser 10, particles within the nozzle section will exhibit one of the following two behaviours: travel or ejection. The mapping step identifies these behaviours and correspondingly localizes the ejection and travel regions 13, 15 within the nozzle section.

The inclusion of the sedimentation region 14 upstream of the ejection region 13 prevents multiple cells from falsely being dispensed as they sediment into the ejection region 13 while the droplet dispenser 10 is in between dispensing routines. The sedimentation region 14 can be a dynamic region which is calculated based on the sedimentation velocity which is a function of the apparent particle size along with the time required for image processing and to move the PDC into position for printing.

Step S3 is performed for every new droplet dispenser 10, dispensing parameters or samples (particle suspension) utilized. Thus, a unique map including the ejection region 13 and at least one sedimentation region 14 (each for one particle type) is created for each new dispensing operation, which is used in the subsequent optical feedback test for single particle encapsulation.

Once trained, the cell dispensing operation can commence. The droplet dispenser 10 is positioned in front of the optical system where each individual particle within the droplet dispenser 10 is identified and tracked in real time. For single particle encapsulation, the optical feedback system will selectively identify single particles for printing while accounting for the potential effects which particles upstream of the nozzle may have on the encapsulation outcome.

The practical operation of the dispenser apparatus 100 for depositing single particles on the target 2 starts with step S4, wherein the particle suspension is loaded into the droplet dispenser 10. The droplet dispenser 10 is aligned relative to the collection reservoir 5 and the nozzle camera 30 (see FIG. 3). The droplet dispenser 10 is positioned in front of the nozzle camera 30, which acquires an image of the nozzle section with step S5. The acquired image is aligned with the base line image collected with step S2, and the presence of particles within the nozzle section 12 is detected. Each individual particle within the nozzle section 12 is identified and tracked in real time.

With step S6, the single particle condition of the droplet dispenser 10 is tested. The acquired image of step S5 is examined for testing whether no particles are located in the sedimentation region 14 and one single particle is located in the ejection region 13. If yes, the droplet dispenser 10 is moved to the target 2, and a droplet including the single particle is deposited on the target 2 with step S7. If not, e.g. if no or multiple particles are present within the ejection region 13, the current droplet to be dispensed is discarded with step S8 by operating the droplet dispenser at the collection reservoir 5. After step S8, the next image is acquired with step S5, followed by another test with step S6.

Advantageously, the inclusion of the sedimentation region 14 upstream of the ejection region 13 prevents multiple particles from falsely being dispensed as they sediment into the ejection region 13 while the droplet dispenser 10 is in between dispensing routines. During the dispensing operation, the optical feedback system can dynamically update the map, in particular the identification of the ejection region 13 if necessary to compensate for any shifts in the dispensing parameters, e.g. shifts in droplet volume.

The sedimentation region 14 can be modelled as static or dynamic region as mentioned above. The dynamic sedimentation region can be calculated based on the expected sedimentation distance of each identified particle to account for the inherent polydisperse particle size range. This may be important as the sedimentation velocity has an exponential relationship with the particle diameter D. Alternatively, the static sedimentation region 14 would be utilized if a preset approximation of the maximum sedimentation distance expected within the droplet dispenser 10 would be sufficient for the particular deposition task.

After step S7, another test can be conducted with step S9, wherein it is tested whether all fields on the target 2 are spotted. If yes, the procedure stops. If not, the droplet dispenser 10 is moved again to the collection reservoir 5 and the nozzle camera 30 (step S10) for acquiring the next image with step S5.

Advantageously, the optical feedback system of the invention enhanced by the mapping pre-process and the consideration of the upstream particle's motions in the sedimentation region 14 allows for a reliable single particle dispensing platform with minimized false positive droplets.

A test printing was performed using HeLa cells suspended at 150.000 cells/ml with an average diameter of 18 μm. Imaging of the grid post-dispensing (top view in FIG. 4) shows that each droplet 4 encapsulated one single cell 1.

The method of FIG. 3 can be modified by adding a negative control mode in order to measure the single cell impurity of a sample. This is valuable e.g. for genomic sequencing applications as it allows for the measurement of the ambient DNA/RNA content of a solution to access the validity of the data from a sequencing run. In a suspended cell solution the major contribution of ambient DNA/RNA would originate from lysed or dead cells.

The negative control mode could be introduced between steps S5 and S6, including a first test whether the negative control mode is to be conducted and, if yes, a second test whether no cells are in the sedimentation region and no cells are in the ejection region. If not, the droplet is discarded, and if yes, the droplet is dispensed as a reference sample which is known to be empty of cells instead of a single cell. Therefore, the printing condition for a negative control would be an ejection and sedimentation region which is empty of any cells.

Furthermore, the method of FIG. 3 can be modified if geometric features of the cells are detected with the nozzle camera 30 and associated image processing software. The single cell condition (step S6 in FIG. 3) to print can be defined as a single cell within the ejection region, no cells within the sedimentation region and a circularity and elongation and area factor within the acceptable region of the geometric decision boundary.

The features of the invention disclosed in the above description, the drawings and the claims can be of significance both individually as well as in combination or subcombination for the realization of the invention in its various embodiments.

What is claimed:

1. A method of depositing droplets of a particle suspension via a droplet dispenser into a collection reservoir or onto a target wherein,
   the droplet dispenser has a suspension reservoir, a nozzle and a drive unit, disposed on the nozzle,
   the droplet dispenser is capable of a dispensing operation wherein, by operating the drive unit, the particle suspension flows from the suspension reservoir through the nozzle towards a terminal opening of the nozzle and droplets of the particle suspension are dispensed through the terminal opening,
   the droplet dispenser is arranged such that all particles of the particle suspension are capable of moving from the suspension reservoir through the nozzle towards the terminal opening by the effect of gravity sedimentation,
   a nozzle camera is arranged for a particle detection including detecting particles in the particle suspension within the nozzle,
   a controller is arranged in electronic communication with the nozzle camera,
   the droplet dispenser and the target are capable of a movement, including moving the droplet dispenser relative to the target or moving the target relative to the droplet dispenser, so that the droplet dispenser is above the target, and the droplet dispenser is capable of the dispensing operation above the target, and
   an operational delay time interval of the droplet dispenser is a time interval between the particle detection and the dispensing operation above the target, including a duration of said movement,
   the method comprising:
   loading the particle suspension into the suspension reservoir of the droplet dispenser;
   after loading the particle suspension, waiting a time period in which particles in the particle suspension sediment from the suspension reservoir and into the nozzle;
   detecting, via the nozzle camera, particles in the particle suspension within the nozzle, said detecting of particles comprising:
   determining nozzle regions, via the controller, the regions including:
      a travel region of the nozzle fluidly connected to and disposed downstream of the suspension reservoir, the travel region being a portion of the nozzle within which particles in the particle suspension how along a longitudinal axis of the nozzle without being dispensed through the terminal opening during dispensing of a single droplet by the drive unit;
      a sedimentation region of the nozzle, which is a downstream section of the travel region; and
      an ejection region of the nozzle disposed downstream of and abutting the sedimentation region, an end of the ejection region disposed opposite the sedimentation region and defining the terminal opening, the ejection region being a portion of the nozzle within which all particles in of the particle suspension currently included within said ejection region are ejected during dispensing of a single droplet by the drive unit, the terminal opening being located below the travel and sedimentation regions and at a lower end of the nozzle;
      wherein the sedimentation region is a portion of the nozzle within which all particles in the particle suspension, when detecting particles, are capable of moving, by the effect of sedimentation, into the ejection region during the operational delay time interval;
   determining, via the controller and the nozzle camera, whether a single particle condition exists, the single particle condition occurring when the particle suspension within the ejection region contains a single particle and the particle suspension within the sedimentation region is free of particles; wherein
      when the single particle condition exists, executing the dispensing operation by moving the droplet dispenser or the target, which moving corresponds to the operational delay time interval, and dispensing, via the drive unit, a droplet of the particle suspension out of the terminal opening of the nozzle onto the target; and
      when the single particle condition does not exist, and either the particle suspension within the ejection region contains more than a single particle or the particle suspension within the sedimentation region contains at least one particle, dispensing, via the drive unit, a droplet of the particle suspension out of the terminal opening of the nozzle into the collection reservoir.

2. The method according to claim 1, further comprising:
   collecting image data of the ejection region and the sedimentation region via the nozzle camera; and
   storing the collected image data in a testing unit coupled with the droplet dispenser.

3. The method according to claim 1,
   wherein the droplet dispenser is located at a position above the collection reservoir during the step of detecting the particles, including while determining the nozzle regions and determining whether a single particle condition exists.

4. The method according to claim 1, wherein determining whether a single particle condition exists includes:
   detecting particles by imaging the nozzle using the nozzle camera, and
   recognizing, via image-analysis software running in the controller, particles in the sedimentation and ejection regions; and
   wherein recognizing the particles in the sedimentation and ejection regions is performed by the controller.

5. The method according to claim 1, further comprising the steps of:
   detecting a single particle condition;
   moving the droplet dispenser between the collection reservoir and the target using a movable dispenser head, to which the droplet dispenser is attached;
   dispensing a droplet onto the target in response to the detection of the single particle condition; and
   collecting images of the target via a head camera attached to the dispenser head; and
   to checking dispensing results via the collected images.

6. The method according to claim 1, wherein when a single particle condition exists, the method further comprises:
   detecting at least one geometric feature of the single particle in the ejection region; and
   determining whether the single particle in the ejection region has at least one of a predetermined circularity, a predetermined elongation, and a predetermined area factor.

7. The method-according to claim 1, wherein the single particles loaded into the suspension reservoir comprise at least one of biological cells, cell aggregates, cell organelles, and synthetic particles.

8. The method accordingly to claim 1 wherein the step of determining nozzle regions comprises:

mapping the nozzle via the controller; and determining the sedimentation region based at least in part on the mapping.

9. The method according to claim 8, wherein mapping the nozzle comprises:

dispensing a series of training droplets of the particle suspension to train the droplet dispenser; and wherein for each training droplet, particles within the training droplet are tracked and identified as either traveling within the nozzle or being ejected out of the terminal opening of the nozzle during dispensing of each of the training droplets.

10. The method of claim 9, wherein determining the sedimentation region comprises:

performing a single calculation based at least in part on a single set of parameters for the particle suspension, and further based at least in part on the operational delay.

11. The method of claim 9, wherein determining the sedimentation region comprises:

performing a plurality of calculations based at least in part on a changing set of parameters for the particle suspension and the operational delay.

* * * * *